United States Patent
Lex

(10) Patent No.: US 8,260,004 B2
(45) Date of Patent: Sep. 4, 2012

(54) METHOD AND APPARATUS FOR THE QUANTITATIVE DETERMINATION OF SURFACE PROPERTIES

(75) Inventor: Konrad Lex, Koenigsdorf (DE)

(73) Assignee: BYK-Gardner GmbH (DE)

( * ) Notice: Subject to any disclaimer, the term of this patent is extended or adjusted under 35 U.S.C. 154(b) by 966 days.

(21) Appl. No.: 12/053,518

(22) Filed: Mar. 21, 2008

(65) Prior Publication Data

US 2008/0232646 A1    Sep. 25, 2008

(30) Foreign Application Priority Data

Mar. 22, 2007   (DE) .................... 10 2007 014 475

(51) Int. Cl.
*G06K 9/00*   (2006.01)
*G01N 21/00*  (2006.01)
(52) U.S. Cl. .................................. 382/108; 356/237.2
(58) Field of Classification Search .................... 382/108
See application file for complete search history.

(56) References Cited

U.S. PATENT DOCUMENTS

| | | | | |
|---|---|---|---|---|
| 6,876,445 | B2* | 4/2005 | Shibuya et al. | 356/237.2 |
| 7,061,602 | B2* | 6/2006 | Hamamatsu et al. | 356/237.2 |
| 2002/0048022 | A1* | 4/2002 | Schmelzer | 356/425 |
| 2003/0197855 | A1 | 10/2003 | Jung et al. | |
| 2004/0036863 | A1* | 2/2004 | Matsusita et al. | 356/237.2 |
| 2004/0252308 | A1* | 12/2004 | Prakash et al. | 356/445 |

OTHER PUBLICATIONS

Official Action dated Aug. 17, 2011 issued in related U.S. Appl. No. 12/053,497 (13 pgs).
Official Action dated Jan. 20, 2012, issued in U.S. Appl. No. 12/053,497, filed Mar. 21, 2008.

* cited by examiner

*Primary Examiner* — David Zarka
(74) *Attorney, Agent, or Firm* — Hayes Soloway P.C.

(57) ABSTRACT

The present disclosure relates to a method for the quantitative determination of surface properties, wherein a spatially resolved image of a surface to be analysed, which contains a large number of measured values, is recorded. In a first method step, the measured values are analysed in order to determine those surface areas which have a specific physical property. A result value of this physical property is then determined, wherein this result value is characteristic of the values of the physical property of all those surface areas of the image determined by analyzing the image. According to the disclosure, the result value is displayed against the size of the determined surface areas.

18 Claims, 2 Drawing Sheets

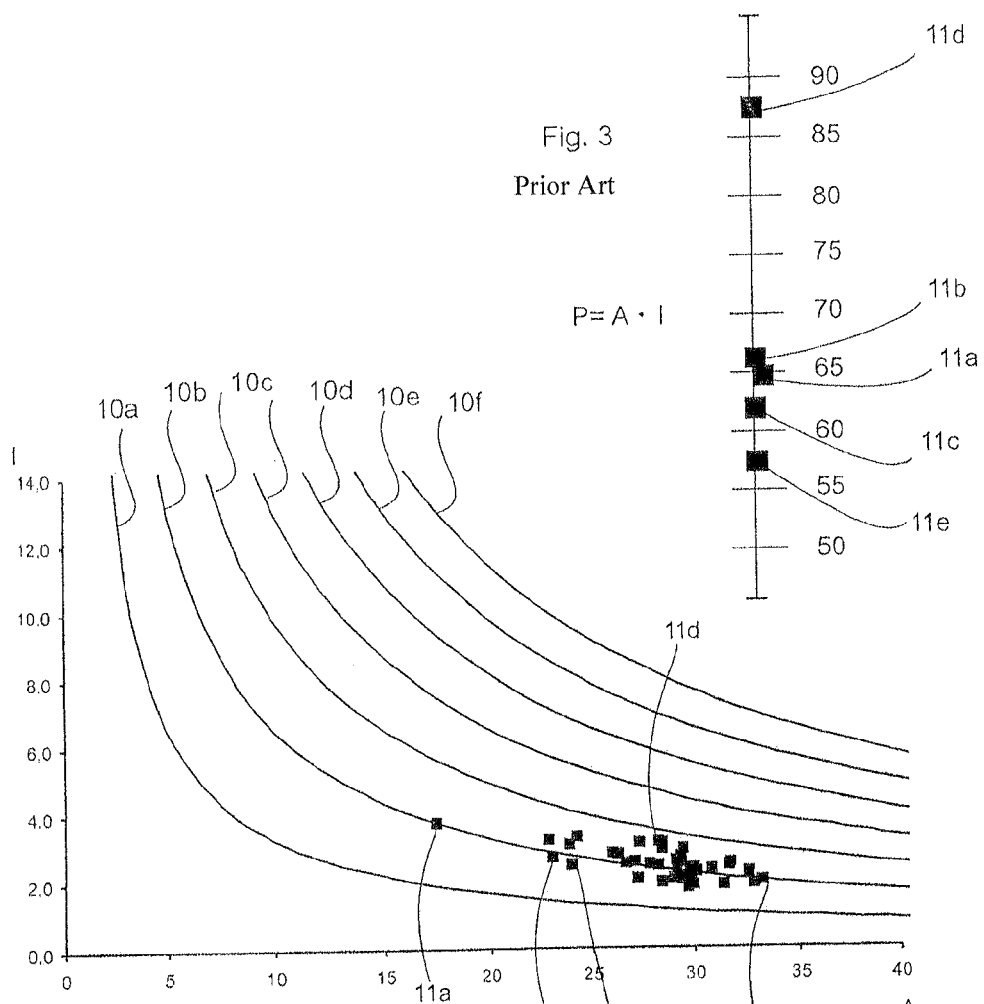
Fig. 3 Prior Art
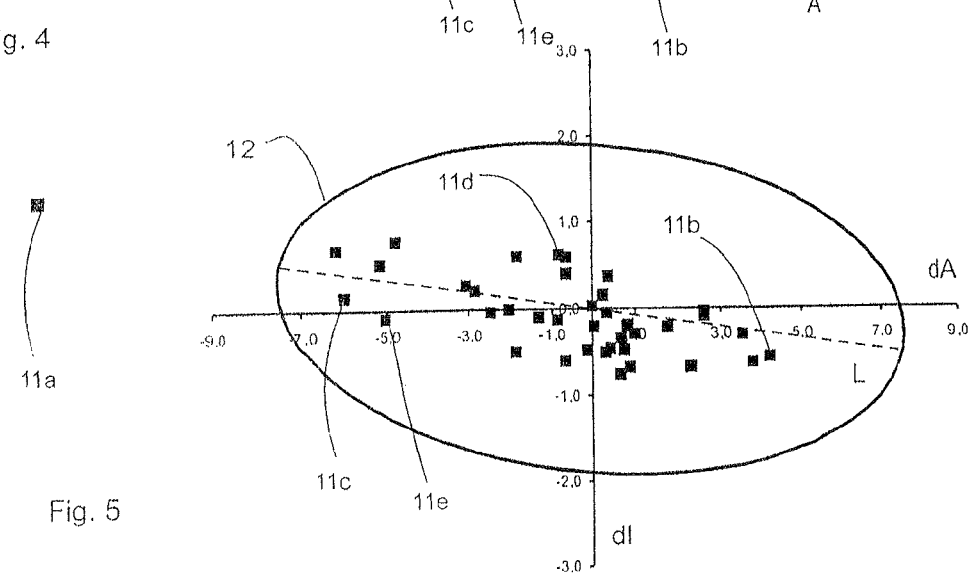
Fig. 4
Fig. 5

METHOD AND APPARATUS FOR THE QUANTITATIVE DETERMINATION OF SURFACE PROPERTIES

BACKGROUND OF THE INVENTION

1. Field of the Invention

The present invention relates to a method and an apparatus for the quantitative determination of surface properties.

The nature of surfaces is an important property of day-to-day objects, such as motor vehicles and other useful objects for example, and determines to a large extent the overall impression given to the human observer. One example includes the high-gloss or metallic coatings on vehicle bodies.

In the context of the invention, surface properties are understood to mean in particular those physical properties of a surface which determine how a surface looks to a human observer. In particular, these include properties such as macrostructure and microstructure, topography, colour, colour point, brightness of the colour, gloss, image sharpness, haze, surface texture, roughness and "orange peel" effect or coarseness.

In order to reproducibly evaluate the quality of surfaces, particularly of these high-gloss coatings, measuring devices are required which detect specifically those physical parameters that determine to a significant extent the overall impression given to a human observer.

2. Description of Related Art

Recently, so-called effect pigment coatings have been gaining increasing popularity. These coatings contain effect pigments which reflect in different ways the light irradiated onto them. From the prior art, apparatuses and methods are known for quantitatively assessing even such effect pigment coatings.

In one known method, for example, a given threshold value for an intensity of the reflected light is defined, and only those surface regions of an observed surface which have an intensity above this threshold value are taken into account. The measurement result is integrated across the respective intensities of the individual surface segments taken into account. This evaluation provides a clue about the optical properties of the surface analysed. However, it has been found that even surfaces which have identical or similar result values from this evaluation can act in very different ways when looked at directly by the human eye.

The object of the present invention is therefore to allow a more accurate classification of surfaces to be analysed.

SUMMARY OF THE INVENTION

In the method according to the invention for the quantitative determination of surface properties, a spatially resolved image of a surface to be analysed is evaluated, wherein this spatially resolved image contains a large number of measured values. This image is analysed in order to determine those surface areas of the surface to be analysed which have or represent a specific physical property that can be characterised in particular by the measured values. Furthermore, a result value of this physical property is determined, wherein this result value is characteristic of the measured values of the physical properties (precisely) of all those surface areas determined by analysing the image. According to the invention, the result value is displayed or output against the size of the determined surface areas.

This result value shown against the size of the determined surface areas need not necessarily be output directly to the user; it is also possible that a processor processes a large number of such results and compares them in an internal comparison in order then to output for example a result of this comparison to the user. In this case, for example, a warning signal may be output to the user as the result of this comparison, which warning signal indicates that a presently measured region of the surface to be analysed is no longer acceptable or can be optically distinguished from other surface areas by an observer.

In other words, a large number of measured values which represent characteristic properties of the surface are recorded in a spatially resolved manner. The image is composed in particular of a large number of pixels, wherein each of these pixels can be assigned at least one specific measured value.

In this connection, reference is made to the further U.S. patent application Ser. No. 12/053,497 filed by the applicant at the same time as the present application and bearing the title "Determination of surface properties". The content of the disclosure of said application is hereby fully incorporated by way of reference into the content of the disclosure of the present application.

Preferably, the result value is obtained by forming a mean of the values of the physical properties of all those surface areas determined by analysing the image. However, integrals, distribution functions, sums and similar operations may be formed.

According to the invention, therefore, firstly those surface areas which have the specific physical property are determined, for example those surface areas having a scattering intensity above a given threshold value. A mean is then formed across the determined intensity values, wherein here only those surface areas which have intensities above said threshold are taken into account. As a result, preferably a relative intensity value is output, i.e. the threshold value is subtracted from the determined intensity value.

Said result value, i.e. the mean intensity value, is then displayed against the size of the determined surface areas. The size of the determined surface areas is obtained in particular by determining the number of pixels represented by those surface areas having an intensity above the threshold value. More specifically, an illuminated area is imaged onto a camera for example and the latter in turn outputs a corresponding spatially resolved image.

While in the prior art an integrative method is used, in which as it were a product of the result value and the associated surface area is output, it is proposed according to the invention to output separately both the size of the surface areas and the result values. This idea is based on the knowledge that for example a high number of pixels or a large surface area with a low intensity has a different effect when looked at compared to a small surface area with a high intensity, and at the same time the respective product can be identical and thus no measurable difference between these two types of surface is output using the method known from the prior art.

Preferably, the image to be evaluated is produced in that radiation is emitted onto the surface to be analysed and at least a proportion of the radiation thrown back from the surface is received by a radiation detector device and this radiation detector device outputs the measured values or the data characteristic of the measured values. The radiation detector device may be for example a CCD chip which receives the radiation and outputs corresponding measured values. It is possible here that firstly an image is recorded and this image is processed in the manner according to the invention directly after being recorded.

Preferably, the mean is taken from a group of means comprising arithmetic means, geometric means, integrals, weighted means, combinations thereof and the like.

Preferably, the physical property is an intensity and in particular a threshold intensity. However, it would also be possible to carry out the method with reference to other physical parameters, such as for example the colour or the like. More specifically, each individual pixel of the recorded image is assessed with regard to the intensity that it displays, so that on the whole the method according to the invention is not an integrative method but rather a differential method.

Preferably, the size of those surface areas is determined which corresponds to a specific value range of this characteristic property. More specifically, as mentioned above, a given threshold value is defined and the lower limit of this value range is the aforementioned threshold value, so that only those surface areas of the observed surface which lie above this characteristic threshold value are taken into account. In this case, specific digital values, for example 1024 different values, are assigned to the determined actual intensity values during the processing of the image.

In another advantageous method, for a large number of spatially resolved images, the result value is plotted against the size of the determined surface area preferably in the same diagram. A large number of individual recordings can thus be carried out over a relatively large surface, and the individual recordings can in each case be plotted in the diagram. From this overall diagram, it is then possible to determine which of the individual subareas of the surface to be analysed lie within a predefined tolerance range, and which lie outside this range. A tolerance value can also be defined on the basis of a large number of spatially resolved images. It is thus possible for example for an image recorded on a fuel tank cap to be compared with one or more images recorded on the hood.

More specifically, for a number of recorded images, the result values are plotted against the size of the surface areas and it is ascertained, based on a comparison, whether the corresponding surfaces give the same optical impression to the observer.

In a further advantageous method, in the diagram, a tolerance zone is defined which determines whether certain predefined sub-areas meet previously set tolerance criteria. It is thus possible to assess for example whether certain regions of a radiator hood paint coating can or cannot be tolerated. The tolerance zone is preferably an ellipse.

Preferably, the tolerance zone is determined using a large number of result values. However, it is also possible that the tolerance zone is defined beforehand, for example by manufacturer's specifications or the like. The tolerance zone may also be defined using a large number of surface area sizes. With particular preference, a certain tolerance region with regard to the surface area sizes is defined along with a certain tolerance region with regard to the result values, and the tolerance zone is formed taking account of both tolerance regions. In order to form the tolerance zone, it is also possible to start from a reference area or from predefined values for the size of the surface areas and the result value.

In a further advantageous method, in the diagram, orientation lines are indicated which symbolise different properties of the surfaces to be analysed. For example, these orientation lines may be lines which symbolise in each case constant products of the surface area sizes and the result value or corresponding, indirectly classified proportionalities. Preferably, therefore, the orientation lines are in each case characteristic of a product value which is obtained from the result value and the size of the surface areas. A rough classification into different surface types is possible via these orientation lines.

Preferably, the surfaces to be analysed are coatings containing effect pigments. However, it would in principle also be possible to analyse other types of coating using the method according to the invention.

In addition, preferably a further value characteristic of the surface is shown in the diagram. This value may be for example a value regarding the structuring of the surface or the so-called coarseness. This coarseness is an indication as to how certain surface properties are repeated, or how certain surface properties act as a function of the viewing distance. In order to represent the coarseness, it is possible to display for example a statistical parameter for example relative to a given resolution. In this connection, reference is made to the German patent application DE 103 24 104 A1 by the applicant, the content of the disclosure of which is hereby incorporated by way of reference into the subject matter of the present description.

It is thus possible for example to plot a variance or scattering of different intensity values on a further axis against the respective surface areas or measurements. In this way, the individual surface areas or measurements can also be characterised with regard to their coarseness. As mentioned above, a mean of the individual intensities is in each case output as the result value. Advantageously, therefore, in addition to the mean, also e.g. a variance or scattering is output which in turn allows conclusions to be drawn about the intensity distributions in the individual observed surface regions.

This further parameter such as the variance may represent for example the contrast of a recorded image or the coarseness thereof. Furthermore, it is also possible to differentiate the effect pigments according to further characteristic features, such as e.g. the colour thereof. Instead of introducing another axis, individual measurement points could also be differentiated from one another in some other way, for example by a different colouring of the measurement points.

In a further advantageous method, the position of the tolerance zone results from at least one of the orientation lines. More specifically, the long half-axis of the tolerance zone formed as an ellipse is matched to the slope of the orientation line at a predefined point. This will be explained in more detail with reference to the figures.

The present invention also relates to an apparatus for the quantitative determination of surface properties, wherein the apparatus comprises a radiation device which directs radiation onto a surface to be analysed, and a radiation detector device which receives the radiation thrown back from the surface and outputs a spatially resolved image which corresponds to the radiation thrown back. Here, too, the surface is imaged onto the radiation detector device.

According to the invention, the apparatus has a processor device which determines those surface areas which have a specific physical property and determines a result value which is characteristic of the physical properties of those surface areas which have the specific physical property. Also provided is an output device which outputs the result value preferably against the size of the determined surface areas. The output device may in the simplest case be a printer device which outputs a two-axis diagram. However, a corresponding diagram can also be output on a monitor or the like.

However, it is also possible that the result values and the size of the surface areas are evaluated only internally, and these values are compared for a number of surface regions. The apparatus according to the invention could also be used for example to carry out a measurement at different points of a coating and to indicate to the user whether two different surface regions give an observer the same optical impression. The specific physical property is preferably an intensity.

Furthermore, the method according to the invention and the apparatus according to the invention may also be used to catalogue the individual displayed measured values, in order to find specific surface types. In this case, it is possible for example to plot the determined result values as a function of a surface area and to compare this for example with a reference table which contains a large number of comparable measurement results. This application is particularly relevant in the motor vehicle repair sector. Furthermore, the invention may be used to produce a specific surface effect or a specific appearance of a surface by means of a specially adapted recipe system. Furthermore, measured values output by the method according to the invention may be used for simulation purposes, in particular but not exclusively on the screen.

BRIEF DESCRIPTION OF THE DRAWINGS

Further advantages and embodiments will emerge from the appended drawings, in which:

FIG. 3 shows a corresponding integrative diagram according to the prior art;

FIG. 4 shows a first diagram according to the invention; and

FIG. 5 shows a further diagram according to the invention.

DETAILED DESCRIPTION

Figure 1:
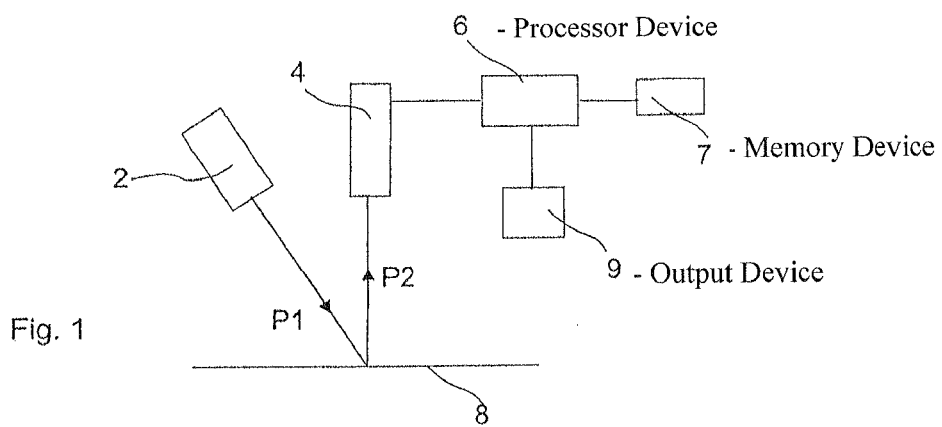
FIG. 1 shows a highly schematic view of an apparatus according to the invention.

FIG. 1 shows a highly schematic view of an apparatus according to the invention for the quantitative determination of surface properties. This apparatus comprises a radiation device 2 which directs radiation, for example light, onto a surface 8 to be analysed. The light thrown back from and in particular scattered and reflected by this surface B is received by a radiation detector device 4. More specifically, the surface is imaged onto this radiation detector device 4, which may comprise for example a CCD chip or a camera. Reference 6 denotes a processor device which evaluates the image recorded by the radiation detector device 4.

This processor device 6 determines, based on a given threshold value, those surface segments for which the respectively impinging radiation exceeds a certain intensity value. In addition, the determined intensity values are also output in digitised form. A mean value is then determined across all those intensity values which lie above the given threshold. This mean value is then the result value to be assessed. In an output device 9, this result value is plotted against the size of the determined surface areas. In addition, a memory device 7 may be provided which stores the respective result values and the sizes of the respective surface areas for a large number of measurements. When indicating the result values, a standardisation may be performed via the average brightness of the sample when irradiated with light. Reference 9 denotes an output device.

Figure 2A:
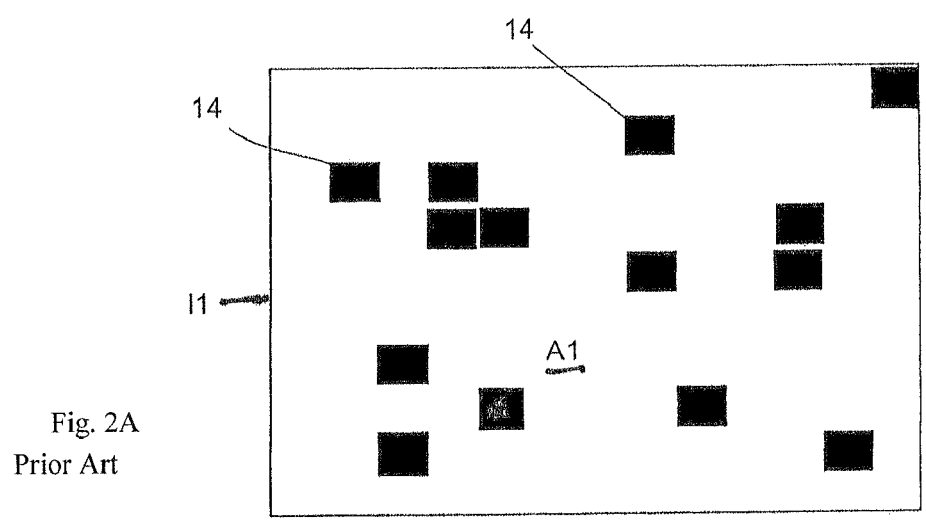
FIGS. 2A and 2B show schematic comparisons of two recorded images.
Figure 2B:
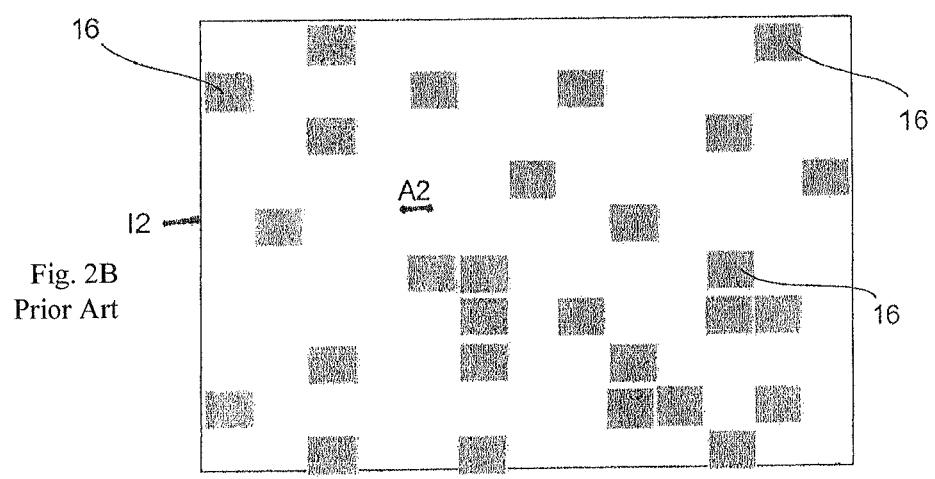

FIG. 2 shows a schematic comparison of two simulated images. In order to illustrate the problem on which the invention is based, only two different intensity values I1 and I2 have been assumed here. In the top part of the image, a determined surface area A1 is obtained as the sum of the surface segments 14, wherein the individual surface segments 14 in each case have or represent the constant uniform intensity value I1. In the bottom part of the image, a corresponding surface area A2 is obtained as the sum of the surface segments 16, wherein here the individual surface segments 16 in each case have the (likewise only theoretical) intensity value I2.

Here, the intensity value I2 is twice as great as the intensity value I1, and conversely the area A1 is twice as large as the area A2. This means that, in the prior art, the output product value I1×A1 would be equal to the value I2×A2 and therefore in the prior art the two surfaces would be regarded as optically identical. However, the fact is that there are considerable differences between the two images, although these cannot be detected by the integrative observation according to the prior art.

FIG. 3 shows a corresponding linear diagram according to the prior art, which likewise shows a plurality of values 11a-11e that have been recorded in different regions of a vehicle, for example on the body, on the wheel arch, on the bumper and the like. With this integral diagram, it can also be seen here that the values all lie in a similar range, which according to the prior art would indicate a similarity of the surfaces. The corresponding values are also marked in the following figures.

FIG. 4 shows a first diagram according to the invention of the measured values shown in FIG. 3 and of further measured values, wherein here the respective result values for the intensity are plotted against surface areas A or the number of pixels. It can be seen here that the measured values which were considered to be equivalent in FIG. 3 can in part be found in very different regions of the diagram. This can be seen in particular when comparing the two values 11a and 11b. While these values lie very close to one another in the integrative diagram in FIG. 3 and thus imply similar surface properties, it can be seen from FIG. 4 that the values are composed of very different result values and surface areas and thus may give very different optical impressions.

The seven marked lines 10a-10f are orientation lines for plotting the diagram according to the invention. Along each individual line, the product of the area A and the intensity I is in each case constant. This means that, with the method from the prior art, points located on this line cannot be differentiated from one another.

In other words, according to the prior art, it is possible to detect only those differences which are different distances away from the marked lines. Since each individual point represents a different measurement, it is clear that measurements recorded at different regions of the motor vehicle in part differ optically from one another to a considerable extent, and that individual surfaces no longer meet the requirements in optical terms. At the same time, therefore, grid areas are defined by the orientation lines 10a-10f.

FIG. 5 shows a further diagram of the intensity against the surface area. Here, however, it is not the intensity and surface area that are indicated but rather the difference value dJ or dA relative to a respective standardised value. Reference 12 denotes a tolerance zone. Measurement points or regions of the surface to be analysed which lie within this tolerance zone are defined as acceptable and cannot be differentiated from one another by the observer. On the other hand, however, surface regions outside this tolerance zone can be perceived as different by the observer.

Here, this tolerance zone 12 is formed in the shape of an ellipse and is to be understood to mean that even measurement points which are at a maximum distance from one another in the tolerance zone shown in FIG. 5, i.e. which lie at opposite ends of the long half-axis L, cannot be distinguished from one another by the observer. By contrast, measured values which lie outside the tolerance zone 12 can be optically distinguished by the observer from those surface areas which lie for example at the directly opposite end of the ellipse. More specifically, for example, the surface regions corresponding to measurement points 11a and 11b can be distinguished optically from one another.

The long axis L of the tolerance ellipse 12 results from the slope of the orientation line 10b of FIG. 4 at a predefined standardisation point. This may be the point (0,0) shown in FIG. 5, i.e. the point of intersection of the two coordinates. However, it is also possible to define this point beforehand on the orientation line in FIG. 4, according to the manufacturer's instructions for example.

Here, the arrangement of the long half-axis according to the slope at the selected point is dependent on the position of this point on the orientation line 10a. If, as shown in FIG. 5, this central point lies in a region with large surface areas and a low intensity, certain fluctuations in the surface areas with regard to their absolute difference will have a lesser effect than corresponding deviations in intensity. This is most apparent when considering that, in FIG. 5, even small intensity fluctuations have a considerable effect on the product, but the differences or fluctuations with regard to the surface areas have only a slight effect on the product.

If the selected central point were to lie for example in a region with small surface areas and a correspondingly high intensity, the long half-axis of the elliptical tolerance zone in FIG. 5 would run much more steeply. In FIGS. 4 and 5, a scale for the coarseness could be plotted on a third coordinate axis. This coarseness, which is also referred to as texture, is another important characteristic aspect of the optical appearance of effect coatings.

A statistical parameter, which is likewise a measure of the intensity distribution of the individual surface regions, may also be output for example on the additional axis. This statistical parameter makes it possible to distinguish whether essentially the same intensities can be found in certain surface regions, or whether these intensities fluctuate greatly in said surface regions. This statistical parameter may be for example a variance or scattering of the individual measured intensity values.

It should be noted here that the spatially resolved observation of the surface which is provided according to the invention in principle makes it possible to ascertain, for each individual pixel of the image recording element, such as a camera, in each case the intensity impinging on said pixel. A large number of these intensities—at least those intensities which lie above the given threshold value—are included in the calculation and said statistical parameter, such as the variance or scattering, is output in addition to the result value.

It is also possible, for example when using a CCD chip, to combine at the outset the signals which correspond to individual image recording elements of this CCD chip. In this way, the resolution of the corresponding chip can be "artificially" varied and thus a further relevant parameter for the impression given by the surface can be obtained.

As mentioned, a corresponding spatially resolved image is evaluated. It is possible here that this spatially resolved image is recorded for example directly before the evaluation, and the evaluation then follows on directly from this. However, it would also be possible firstly to record a large number of spatially resolved images and then to evaluate these. The evaluation of the images may also take place independently of the generation thereof.

All of the features disclosed in the application documents are claimed as essential to the invention in so far as they are novel individually or in combination with respect to the prior art.

LIST OF REFERENCES 2 radiation device
4 radiation detector device
6 processor device
7 memory device
8 surface
9 output device
10a-10f orientation lines
ha-lie values
12 tolerance zone
14, 16 surface segment
I, I1, I2 intensity values
A, A2, A2 surface areas
d1 difference in intensities
dA difference in surface areas
I long half-axis of the tolerance zone 12

The invention claimed is:

1. A method for the quantitative determination of surface properties, wherein a spatially resolved image of a surface to be analysed, which contains a plurality of measured values, is evaluated, said method comprising the steps:
analysing the measured values in order to determine those surface areas (A) of the image which represent a specific physical property that can be characterised by the measured values and
determining a result value (I) of said physical property, wherein said result value is characteristic of the measured values of the physical property of all those surface areas (A) determined by analysing the measured values, on a processor;
wherein the result value (I) is output against the size of the determined surface areas (A), wherein the size of the determined surface areas are obtained by determining the number of pixels represented by those determined surface areas having an intensity above a threshold value, and wherein for a selected plurality of spatially resolved images, the result value is plotted against the size of the determined surface areas (A) in a same diagram, and wherein in the diagram, orientation lines are indicated which symbolise different properties of the surface to be analysed.

2. A method according to claim 1, wherein the result value (I) is obtained by forming a mean of the values of the physical property of all those surface areas (A) determined by analysing the image.

3. A method according to claim 2, wherein the mean is taken from a group of means comprising arithmetic means, geometric means, integrals, weighted means, combinations thereof and the like.

4. A method according to claim 1, wherein the physical property is an intensity.

5. A method according to claim 4, wherein said physical property is a minimum property.

6. A method according to claim 1, wherein the size of those surface areas is determined which characterises a specific value range of a characteristic property.

7. A method according to claim 1, wherein in the diagram, a tolerance zone is defined which determines whether predefined surface areas meet previously set tolerance criteria.

8. A method according to claim 7, wherein the tolerance zone is determined using a plurality of result values.

9. A method according to claim 7, wherein the tolerance zone is defined using a plurality of determined surface area sizes.

10. A method according to claim 7, wherein a further value characteristic of the surface is shown in the diagram.

11. A method according to claim 1, wherein the orientation lines are in each case characteristic of a product value P which results from the result value (I) and the size of the surface areas (A).

12. A method according to claim 1, wherein surfaces to be analysed are coatings containing effect pigments.

13. A method according to claim 1, wherein the position of the tolerance zone results from at least one of the orientation lines.

14. An apparatus for the quantitative determination of surface properties of effect pigment coatings on vehicle bodies, comprising a radiation device which directs radiation onto a surface to be analysed, and comprising a radiation detector device which receives the radiation thrown back from the surface and outputs a spatially resolved image which corresponds to the radiation thrown back, wherein the apparatus has a processor device which determines those surface areas of the surface which have a specific physical property and determines a result value (I) which is characteristic of the physical properties of those surface areas which have the specific physical property, and comprising an output device which outputs the result value and the size of the determined surface areas, wherein the apparatus comprises a memory device, which stores the respective result values and the sizes of the respective determined surface areas for a plurality of measurements, and wherein the processor device based on a comparison ascertains whether the corresponding surface areas give the same optical impression to an observer.

15. A method for the quantitative determination of surface properties of effect pigment coatings, wherein a spatially resolved image of a surface to be analysed, which contains a plurality of measured values, is evaluated, said method comprising the steps:

analysing the measured values in order to determine those surface areas (A) of the image which represent a specific physical property that can be characterised by the measured values; and determining a result value (I) of said physical property, wherein said result value is characteristic of the measured values of the physical property of all those surface areas (A) determined by analysing the measured values, on a processor;

wherein the result value (I) is output against the size of the determined surface areas (A), wherein the size of the surface area is obtained by determining the number of pixels represented by those determined surface areas having an intensity above a threshold value, wherein for a selected plurality of spatially resolved images, the result value is plotted against the size of the determined surface areas (A) in a same diagram, and wherein in the diagram a tolerance zone is defined which determines whether predefined surfaces areas meet previously set tolerance criteria.

16. A method for the quantitative determination of surface properties, wherein a spatially resolved image of a surface to be analysed, which contains a plurality of measured values, is evaluated, said method comprising the steps:

analysing the measured values in order to determine those surface areas (A) of the image which represent a specific physical property that can be characterised by the measured values and determining a result value (I) of said physical property, wherein said result value is characteristic of the measured values of the physical property of all those surface areas (A) determined by analysing the measured values, on a processor;

wherein the result value (I) is output against the size of the determined surface areas (A), wherein the size of the determined surface areas are obtained by determining the number of pixels represented by those determined surface areas having an intensity above a threshold value, and wherein for a selected plurality of spatially resolved images, the result value is plotted against the size of the determined surface areas (A) in a same diagram, and, wherein in the diagram, a tolerance zone is defined which determines whether predefined surface areas meet previously set tolerance criteria.

17. A method according to claim 16, wherein the tolerance zone is determined using a plurality of result values.

18. A method according to claim 16, wherein the tolerance zone is defined using a plurality of determined surface area sizes.

* * * * *